(12) United States Patent
Clarke et al.

(10) Patent No.: US 6,699,650 B1
(45) Date of Patent: Mar. 2, 2004

(54) PHOTOGRAPHIC COUPLERS HAVING IMPROVED IMAGE DYE LIGHT STABILITY

(75) Inventors: David Clarke, Herts (GB); Llewellyn J. Leyshon, Herts (GB); Katie E. Smith, Herts (GB)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/856,396

(22) PCT Filed: Dec. 22, 1999

(86) PCT No.: PCT/GB99/04360

§ 371 (c)(1),
(2), (4) Date: May 22, 2001

(87) PCT Pub. No.: WO00/38013

PCT Pub. Date: Jun. 29, 2000

(30) Foreign Application Priority Data

Dec. 22, 1998 (GB) ............................................. 9828147

(51) Int. Cl.⁷ ............................ G03C 7/46; G03C 7/32; C12Q 1/68
(52) U.S. Cl. ...................... 430/384; 430/385; 430/552; 430/553; 430/558; 435/6; 427/213.3; 264/4.1
(58) Field of Search ....................... 427/213.3, 213.33, 427/213.31, 231.32; 428/402.2, 402.21; 264/4.1; 430/384, 385, 552

(56) References Cited

U.S. PATENT DOCUMENTS 4,124,396 A * 11/1978 Osborn ....................... 430/553
4,299,914 A   11/1981 Fujimatsu et al.
4,362,810 A   12/1982 Usagawa et al.

FOREIGN PATENT DOCUMENTS

GB   2 070 000 A   9/1981
JP   59 069755     4/1984

* cited by examiner

*Primary Examiner*—Jeffrey Fredman
(74) *Attorney, Agent, or Firm*—Arthur E. Kluegel

(57) ABSTRACT

There is provided a photographic element comprising at least one silver halide emulsion layer having associated therewith a novel phenolic cyan dye-forming coupler of formula (I)

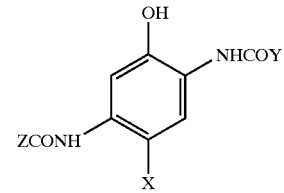

(I)

wherein

X is hydrogen or a group that can be split off by the reaction of the coupler with an oxidised colour developing agent, and one of Y and Z is the group

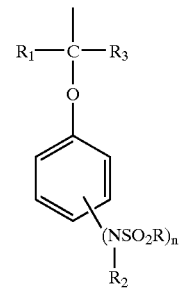

wherein each R is independently an unsubstituted or substituted alkyl or aryl group or a 5–10 membered heterocyclic ring which contains one or more heteroatoms selected from nitrogen, oxygen and sulfur, which ring is unsubstituted or substituted;

$R_1$ is hydrogen or an unsubstituted or substituted alkyl or aryl group, $R_2$ is an unsubstituted or substituted alkyl or aryl group or a 5–10 membered heterocyclic ring which contains one or more heteroatoms selected from nitrogen, oxygen and sulfur, which ring is unsubstituted or substituted;

$R_3$ is hydrogen or an unsubstituted or substituted alkyl or aryl group, n is 1 or 2, and the other of Y and Z is an unsubstituted or substituted alkyl or aryl group or a 5–10 membered heterocyclic ring which contains one or more heteroatoms selected from nitrogen, oxygen and sulfur, which ring is unsubstituted or substituted.

The couplers for use in the element of the invention yield cyan images of good hue, with good stability to heat, humidity and light, whilst retaining the other properties desirable for good photographic performance.

10 Claims, No Drawings

PHOTOGRAPHIC COUPLERS HAVING IMPROVED IMAGE DYE LIGHT STABILITY

FIELD OF THE INVENTION

The present invention relates to a colour photographic element containing a novel phenolic cyan image dye-forming coupler and in particular a coupler containing an N-alkyl sulphonamide substituent.

BACKGROUND OF THE INVENTION

In silver halide based colour photography, a typical photographic element contains multiple layers of light-sensitive photographic silver halide emulsions coated on a support with one or more of these layers being spectrally sensitised to each of blue light, green light and red light. The blue, green and red light-sensitive layers typically contain yellow, magenta, and cyan image dye-forming couplers, respectively. After exposure to light, colour development is accomplished by immersing the exposed material in an aqueous alkali solution containing an aromatic primary amine colour developing agent. The dye-forming couplers, hereinafter image couplers, are selected so as to react with the oxidised colour developing agent to provide yellow, magenta and cyan dyes in the so called subtractive colour process to reproduce their complementary colours, blue, green and red as in the original image.

The important features for selecting the image coupler include; efficient reaction with oxidised colour developing agent, thus minimising the necessary amounts of coupler and silver halide in the photographic element; the formation of dyes with hues appropriate for the photographic use of interest: for colour photographic paper applications this requires that dyes have low unwanted side absorption leading to good colour reproduction in the photographic print; minimisation of image dye loss contributing to improved image permanence under both ambient illumination and conventional storage conditions; and in addition the selected image coupler must exhibit good solubility in coupler solvents, provide good dispersibility in gelatin and remain stable during handling and manipulation for maximum efficiency in manufacturing processes.

In recent years, a great deal of study has been conducted to improve image couplers for silver halide photosensitive materials in terms of improved colour reproducibility and image dye stability. However, further improvements are needed, particularly in the area of cyan couplers. In general, cyan dyes are formed by the reaction of, generally, phenols or naphthols with oxidised colour developing agents as described, for example, in U.S. Pat. Nos. 2,367,351, 2,423,730, 2,474,293, 2,772,161, 2,772,162, 2,895,826, 2,920,961, 3,002,836, 3,034,892, 3,041,236, 3,466,622, 3,476,563, 3,552,962, 3,758,308, 3,779,763, 3,839,044, 3,880,661, 3,998,642, 4,214,396, 4,299,914, 4,362,810, 4,333,999, 4,883,746, 4,990,436, 4,960,685, 5,476,757 and 5,614,357; in French Patent Nos. 1,478,188 and 1,479,043, in UK Patent No. 2,070,000 and "Farbkuppler—Eine Literature Ubersicht," published in Agfa Mitteilungen, Band III, pp. 156–175 (1961). Also useful are the cyan couplers described in, for instance, European Patent Application Nos. 544,322; 556,700; 556,777; 565,096; 570,006; and 574,948 and JP-A-59069755.

These types of image couplers can be used either by being incorporated in the photographic silver halide emulsion layers or externally in the processing baths. In the former case the couplers must have ballast substituents built into the molecule to prevent the couplers from migrating from one layer into another. Although these couplers have been used extensively in colour photographic film and paper products, the dyes derived from them still suffer from poor stability to heat, humidity or light, low coupling efficiency or optical density, and in particular from undesirable blue and green absorptions which cause considerable reduction in colour reproduction and colour saturation.

2,5-diacylamino phenols are well known in the art of photography, and it is also well known that image dyes derived from them exhibit good resistance to fading by heat and humidity. However their image dyes are deficient in their ability to withstand the effects of light. Moreover, their absorption bands tend to lie at shorter wavelengths than is desirable, particularly for colour paper applications.

It is known that the absorption characteristics of image dyes can be manipulated by incorporating certain functionalities into the molecular structure and that the chemical environment in which the dye is situated can also influence the hue of the dye. For example, U.S. Pat. No. 5,376,519 and JP 5,9171,953 teach the use of certain phenolic coupler solvents to shift the dye absorption band to longer wavelengths.

PROBLEM TO BE SOLVED BY THE INVENTION

There is still a need to provide a photographic element containing a dispersion of a cyan dye-forming coupler which can provide improved light and dark stability under normal storage conditions, improved colour reproduction in the generation of photographic images and high reactivity for formation of dye with oxidised colour developing agent.

SUMMARY OF THE INVENTION

According to the present invention there is provided a photographic element comprising at least one silver halide emulsion layer having associated therewith a phenolic cyan dye-forming coupler of formula (I)

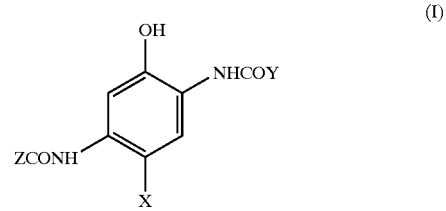

wherein

X is hydrogen or a group that can be split off by the reaction of the coupler with an oxidised colour developing agent, and one of Y and Z is the group

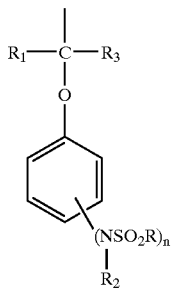

wherein
- each R is independently an unsubstituted or substituted alkyl or aryl group or a 5–10 membered heterocyclic ring which contains one or more heteroatoms selected from nitrogen, oxygen and sulfur, which ring is unsubstituted or substituted;
- $R_1$ is hydrogen of an unsubstituted or substituted alkyl or aryl group,
- $R_2$ is an unsubstituted or substituted alkyl or aryl group or a 5–10 membered heterocyclic ring which contains one or more heteroatoms selected from nitrogen, oxygen and sulfur, which ring is unsubstituted or substituted;
- $R_3$ is hydrogen or an unsubstituted or substituted alkyl or aryl group,
- n is 1 or 2, and each group —$N(R_2)SO_2R$ is in the ortho or para position,
- the other of Y and Z is a fluoro-substituted alkyl group or an unsubstituted or substituted aryl group or a 5–10 membered heterocyclic ring which contains one or more heteroatoms selected from nitrogen, oxygen and sulfer, which ring is unsubstituted or substituted, provided that (a) when $R_2$ is an unsubstituted benzyl group, n is 1 and —$N(R_2)SO_2R$ is in the ortho position, R may not be a pyridyl group, and (b) at least one of R, $R_1$, $R_2$, X and Y or Z is or includes a ballast group.

In another embodiment of the invention there is provided a multicolour photographic element comprising a support bearing yellow, magenta and cyan image-dye-forming units comprising at least one blue-, green- or red-sensitive silver halide emulsion layer having associated therewith at least one yellow, magenta or cyan dye-forming coupler respectively, wherein the element comprises at least one cyan dye-forming coupler of formula (I) as herein described.

In yet another embodiment of the invention there is provided a process of forming an image in a photographic element as hereinbefore defined after the element has been imagewise exposed to light, comprising contacting the element, as herein described, with a colour developing agent.

In a further embodiment of the invention there is provided a novel coupler of formula (I) as herein described.

ADVANTAGEOUS EFFECT OF THE INVENTION

This invention provides an element which yields a cyan image of good hue, with good stability to heat, humidity and light, whilst retaining the other properties desirable for good photographic performance.

DETAILED DESCRIPTION OF THE INVENTION

As used herein and throughout the specification unless where specifically stated otherwise, the term "alkyl" refers to an unsaturated or saturated, straight or branched chain alkyl group, including alkenyl and aralkyl, and includes cyclic alkyl groups, including cycloalkenyl, having 3–8 carbon atoms and the term "aryl" includes specifically fused aryl. The term "low alkyl" refers to an alkyl group having up to 6 carbon atoms, preferably up to 4 carbon atoms.

In a preferred embodiment of the invention R, $R_1$ and $R_2$ are independently an unsubstituted or substituted alkyl group, with at least one of these normally being a ballast group having at least 8 carbon atoms to render the coupler substantially nondiffusible from the layer in which it is coated. More preferably R and $R_2$ are lower allyl groups, especially methyl or ethyl, and the ballast is provided in $R_1$, which may desirably contain at least 12 carbon atoms. Desirably $R_3$ is a hydrogen atom. Preferably n is 1 and the —$N(R_2)SO_2R$ group is in the para position although it is possible for there to be one or two such groups in the ortho positions.

Preferably the group Z contains the —$N(R_2SO_2R)$ substituent and the group Y is suitably an unsubstituted or substituted aryl group, which may provide a ballast residue, an is especially a phenyl group substituted, for example with one or more chloro, fluoro, trifluoromethyl, cyano, alkoxycarbonyl or alkylsulfonyl groups or it may be a naphthyl, pyridyl or a fluoro-substituted alkyl group.

Couplers can be defined as being 4-equivalent or 2-equivalent depending on the number of atoms of Ag+ required to form one molecule of dye. A 4-equivalent coupler can generally be converted into a 2-equivalent coupler by replacing a hydrogen at the coupling site with a different coupling-off group. Coupling-off groups are well known in the art. Such groups can modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation or colour correction. Representative classes of such coupling-off groups include, for example, chloro, alkoxy, aryloxy, heterooxy, sulfonyloxy, acyloxy, acyl, heterocyclyl, sulfonamido, mercapto-tetrazole, benzothiazole, alkylthio (such as mercaptopropionic acid), arylthio, phosphonyloxy and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in U.K. Patents and published application Nos. 1,466,728, 1,531,927, 1,533,039, 2,006,755A and 2,017,704A, the disclosures of which are incorporated herein by reference. Halogen, alkoxy and aryloxy are most suitable.

Examples of suitable coupling-off groups are —Cl, —F, —Br, —SCN, —$OCH_3$, —$OC_6H_5$, —$OCH_2C(=O)NHCH_2CH_2OH$, —$OCH_2C(O)NHCH_2CH_2OCH_3$, —$OCH_2C(O)NHCH_2CH_2OC(=O)OCH_3$, —$P(=O)(OC_2H_5)_2$, —$SCH_2CH_2COOH$,

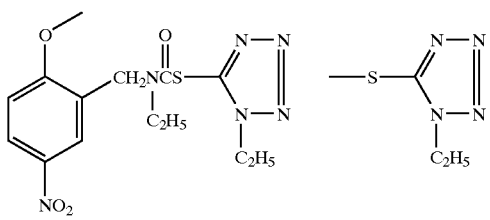

-continued

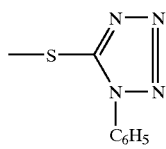
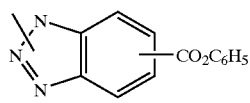

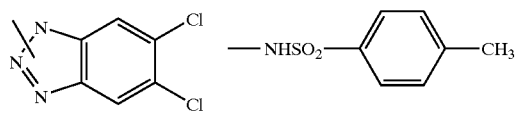

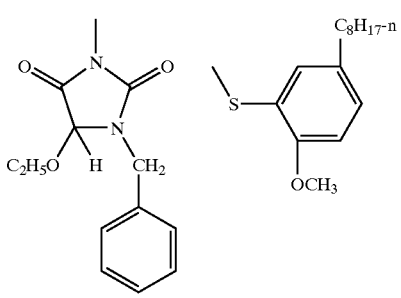

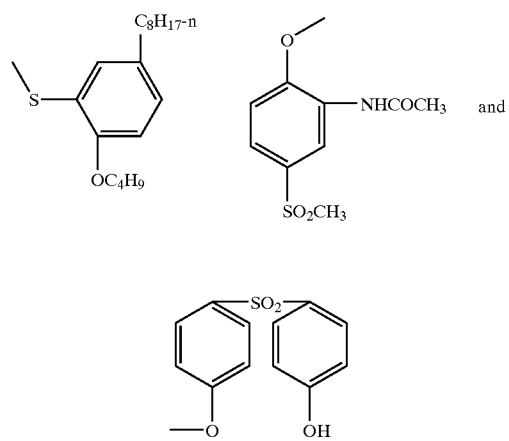

Typically the coupling-off group is a chlorine atom, hydrogen or a p-methoxy-phenoxy group.

It is important that the substituent groups R, R$_1$, R$_2$, X and Y or Z, are selected so as to adequately ballast the coupler and the resulting dye in the organic solvent in which the coupler is dispersed. The ballasting may be accomplished by providing hydrophobic substituent groups in one or more of these substituent groups. Generally a ballast group is an organic radical of such size and configuration as to confer on the coupler molecule sufficient bulk and aqueous insolubility as to render the coupler substantially nondiffusible from the layer in which it is coated in a photographic element. Thus the combination of these substituent groups in the couplers for use in the invention are suitably chosen to meet these criteria. To be effective, the ballast will usually contain at least 8 carbon atoms and typically contains 10 to 30 carbon atoms. Suitable ballasting may also be accomplished by providing a plurality of groups which in combination meet these criteria. Although the coupling-off group X may contains a ballast it is often necessary to ballast the other substituents as well, since X is eliminated from the molecule upon coupling.

The following examples further illustrate the invention. It is not to be construed that the present invention is limited to thee examples:

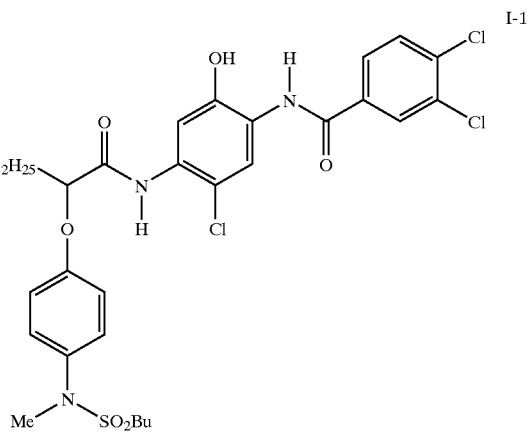

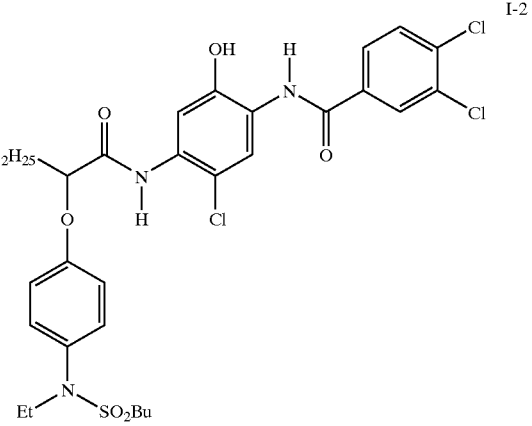

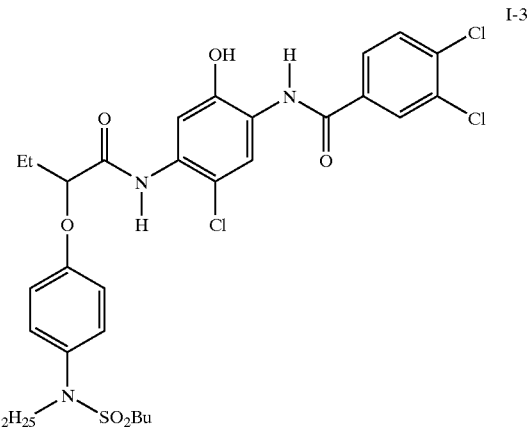

I-4
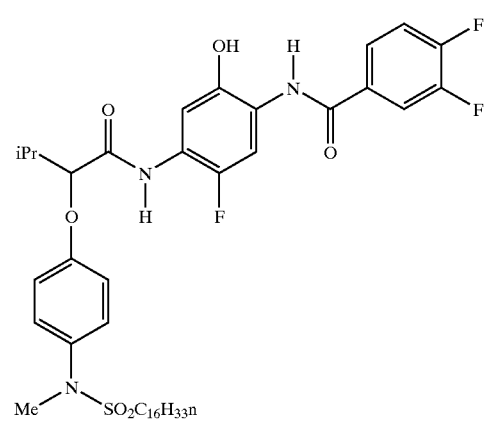
I-5
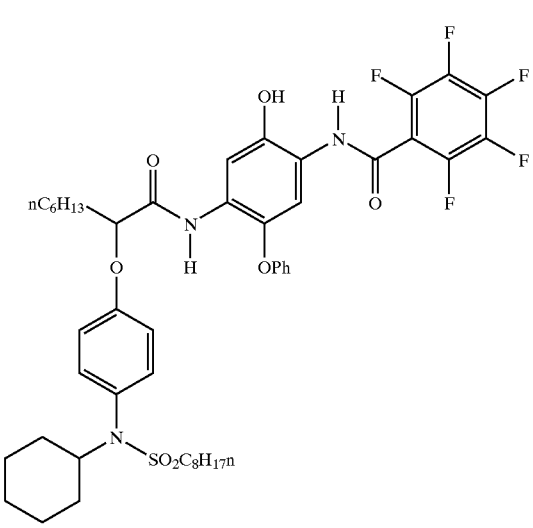
I-6
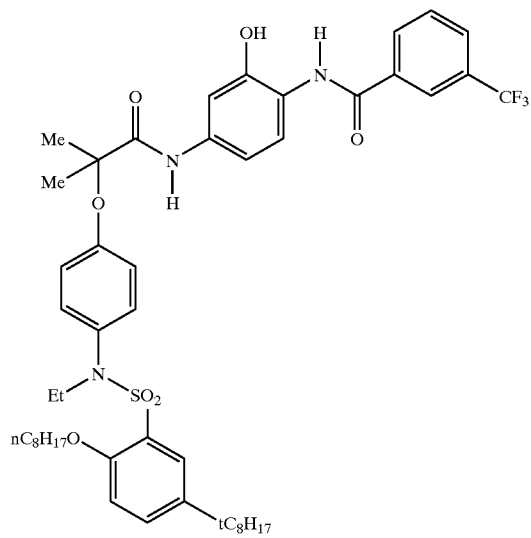
I-7
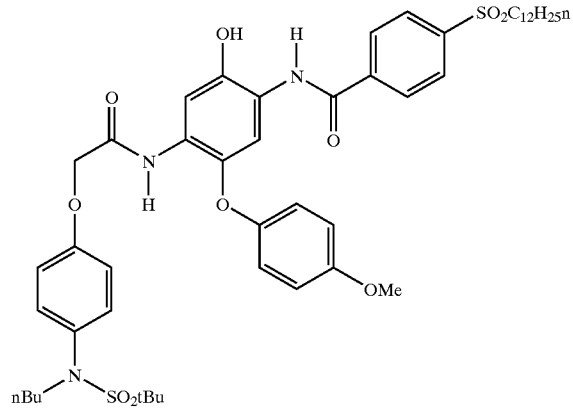
I-8
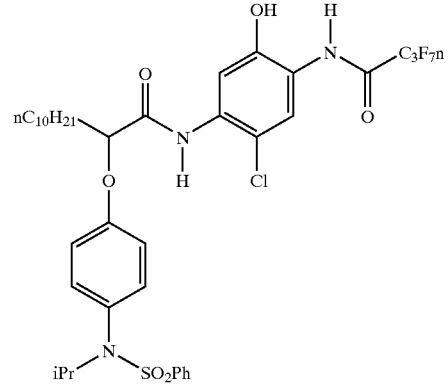
I-9
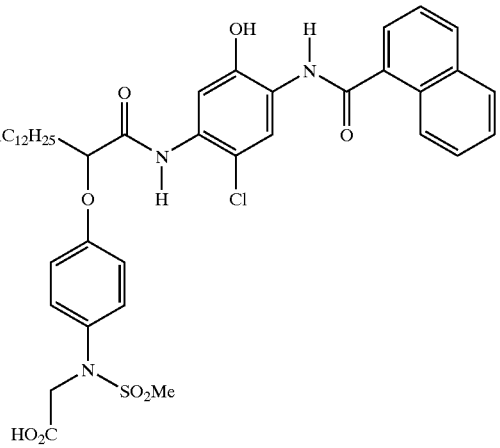
I-13
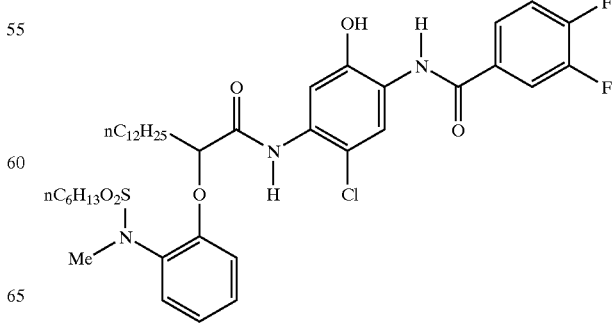

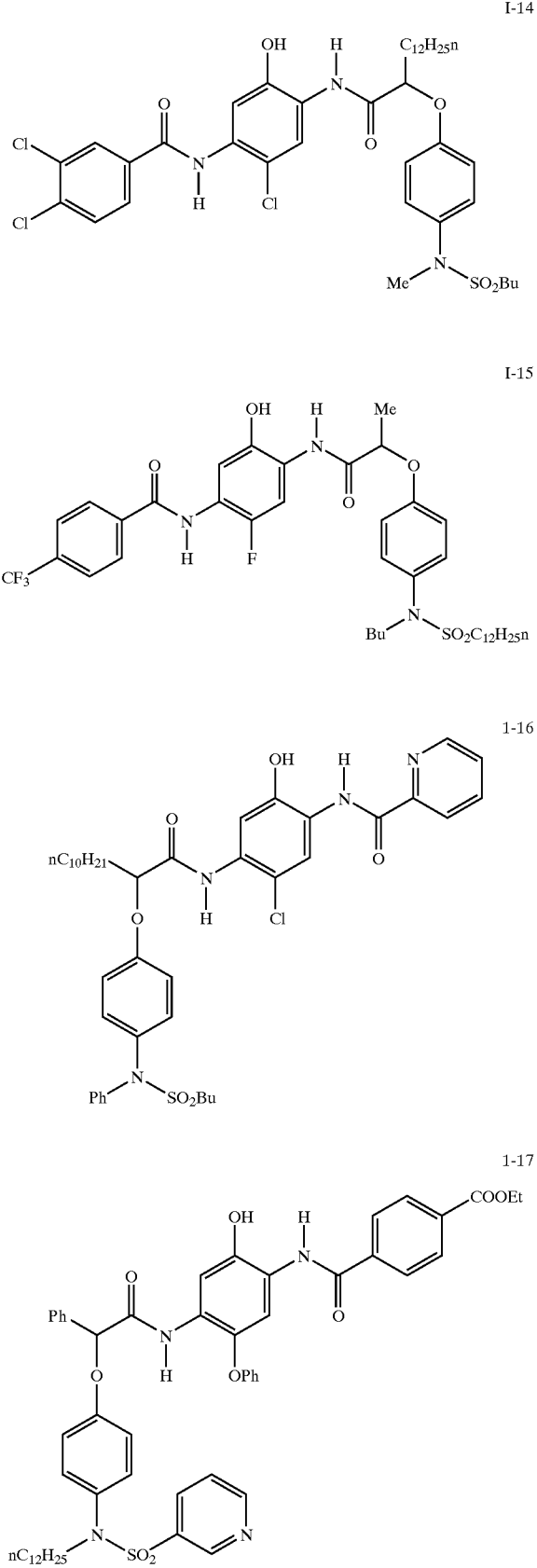

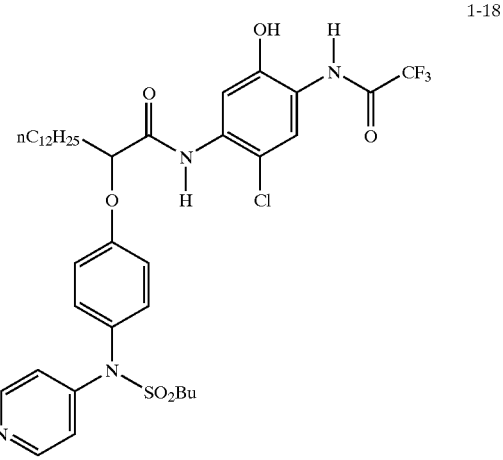

Unless otherwise specifically stated, substituent groups which may be substituted on molecules herein include any groups, whether substituted or unsubstituted, which do not destroy properties necessary for photographic utility. When the term "group" is applied to the identification of a substituent containing a substitutable hydrogen, it is intended to encompass not only the substituent's unsubstituted form, but also its form further substituted with any group or groups as herein mentioned. Suitably, the group may be halogen or may be bonded to the remainder of the molecule by an atom of carbon, silicon, oxygen, nitrogen, phosphorous or sulfur. The substituent may be, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,4-di-t-pentylphenoxy) propyl and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy and 2-dodecyloxyethoxy; aryl such as phenyl, 4-t-butyl-phenyl, 2,4,6-trimethylphenyl, naphthyl; aryloxy, such as phenoxy, 2-methylphenoxy, alpha- or beta-naphthyl-oxy and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy) butyramido, alpha-(3-pentadecylphenoxy)hexanamido, alpha-(4-hydroxy-3-t-butylphenoxy)-tetradecanmido, 2-oxopyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl and N-acetyl-N-dodecylamino, ethoxycarbonylamino, phenoxycarbonylamino, benzyloxycarbonylamino, hexadecyloxycarbonyl-amino, 2,4-di-t-butylphenoxycarbonylamino, phenyl-carbonylamino, 2,5-(di-t-pentylphenyl)carbonylamino, p-dodecylphenylcarbonylamino, p-toluylcarbonylamino, N-methylureido, N,N-dimethylureido, N-methyl-N-dodecyl-ureido, N-hexadecylureido, N,N-dioctadecylureido, N,N-dioctyl-N'-ethylureido, N-phenylureido, N,N-di-phenylureido, N-phenyl-N-p- toluylureido, N-(m-hexadecylphenyl)ureido, N,N-(2,5-di-t-pentylphenyl)-N'-ethylureido and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropylsulfamoylamino and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]-sulfamoyl N-methyl-N-tetradecyl-sulfamoyl and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]-carbamoyl, N-methyl-N-tetradecylcarbamoyl and N,N-di-octylcarbamoyl; acyl, such as acetyl, (2,4-di-t-amyl-phenoxy)acetyl, phenoxycarbonyl, p-dodecyloxyphenoxy-carbonyl, methoxycarbonyl, butoxycarbonyl, tetradecyl-oxycarbonyl, ethoxycarbonyl, benzyloxycarbonyl, 3-pentadecyloxycarbonyl and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4nonylphenylsulfonyl and p-toluylsulfonyl; sulfonyl-oxy, such as dodecylsulfonyloxy and hexadecylsulfonyl-oxy; sulfinyl, such as methylsulfinyl, octylsulfinyl 2-ethylhexylsulfinyl, dodecylsulfinyl, hexadecyl-sulfinyl, phenylsulfinyl, 4-nonylphenylsulfinyl and p-toluylsulfinyl; thio, such as ethylthio, octylthio, benzylthio, tetradecylthio, 2-(2,4-di-t-pentylphenoxy) ethylthio, phenylthio, 2-butoxy-5-t-octylphenylthio and p-tolylthio; acyloxy, such as acetyloxy, benzoyloxy, octadecanoyloxy,p-dodecylamidobenzoyloxy, N-phenylcarbamoyloxy, N-ethylcarbamoyloxy and cyclohexyl-carbonyloxy; amino, such as phenylanilino, 2-chloro-anilino, diethylamino and dodecylamino; imino, such as 1 (N-phenylimido)ethyl, N-succinimido or 3-benzyl-hydantoinyl; phosphate, such as dimethylphosphate and ethylbutylphosphate; phosphite, such as diethyl and dihexy-lphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups. Generally, the above groups and substituents thereof may include those having up to 48 carbon atoms, typically 1 to 36 carbon atoms and usually less than 24 carbon atoms, but greater numbers are possible depending on the particular substituents selected.

Representative substituents on ballast groups include alky, aryl alkoxy, aryloxy, alkylthio, hydroxy, halogen, alkoxycarbonyl aryloxycarbonyl carboxy, acyl, acyloxy, amino, anilino, carbonamido, carbamoyl alkylsulfonyl, arylsulfonyl, sulfonamido and sulfamoyl groups wherein the substituents typically contain 1 to 42 carbon atoms. Such substituents can also be further substituted.

The material for use in the invention can be used in any of the ways and in any of the combinations known in the art. Typically, the materials are incorporated in a silver halide emulsion and the emulsion coated as a layer on a support to form part of a photographic element. Alternatively, unless provided otherwise, they can be incorporated at a location adjacent to the silver halide emulsion layer where, during development, they will be in reactive association with development products such as oxidised colour developing agent. Thus, as used herein, the term "associated" signifies that the compound is in the silver halide emulsion layer or in an adjacent location where, during processing, it is capable of reacting with silver halide development products.

The photographic elements can be single colour elements or multicolour elements. Multicolour elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the tree primary regions of the spectrum can be disposed as a single segmented layer.

A typical multicolour photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers and subbing layers.

In the following discussion of suitable materials for use in the emulsions and elements that can be used in conjunction with this photographic element, reference will be made to *Research Disclosure*, September 1996, Item 38957, published by Kenneth Mason Publications, Ltd, Dudley House, 12 North Street, Emsworth, Hampshire P010 7DQ, England, which will be identified hereafter by the term "*Research Disclosure*" and the Sections hereafter referred to are Sections of this *Research Disclosure*.

The emulsions can be surface-sensitive emulsions, i.e. emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

Suitable emulsions and their preparation as well as methods of chemical and spectal sensitisation are described in Sections I and II–IV. Vehicles and vehicle related addenda are described in Section II. Dye image formers and modifiers are described in Section X. Various additives such as UV dyes, brighteners, luminescent dyes, antifoggants, stabilizers, light absorbing and scattering materials, coating aids, plasticizers, lubricants, antistats and matting agents are described, for example, in Sections VI–IX. Layers and layer arrangements, colour negative and colour positive features, scan facilitating features, supports, exposure and processing can be found in Sections XI–XX.

Other image dye-forming couplers may be included in the element of the invention, including other couplers that form cyan dyes, such as are hereinbefore described. Preferably such couplers are phenols and naphthols that form cyan dyes on reaction with oxidised colour developing agent.

Couplers that form magenta dyes upon reaction with oxidised colour developing agent are described in such representative patents and publications as: U.S. Pat. Nos. 2,600,788; 2,369,489; 2,343,703; 2,311,082; 2,908,573; 3,062,653; 3,152,896; 3,519,429 and "Farbkuppler—Eine Literature Ubersicht," published in Agfa Mitteilungen, Band III, pp. 126–156 (1961). Preferably such couplers are pyrazolones, pyrazolotriazoles, or pyrazolobenzimidazoles that form magenta dyes upon reaction with oxidised colour developing agents. Especially preferred couplers are 1H-pyrazolo [5,1-c]-1,2,4-triazole and 1H-pyrazolo [1,5-b]-1,2,4-triazole. Examples of 1H-pyrazolo [5,1-c]-1,2,4-triazole couplers are described in U.K. Patent Nos. 1,247,493; 1,252,418; 1,398,979; U.S. Pat. Nos. 4,443,536; 4,514,490; 4,540,654; 4,590,153; 4,665,015; 4,822,730; 4,945,034; 5,017,465; and 5,023,170. Examples of 1H-pyrazolo [1,5-b]-1,2,4-triazoles can be found in European Patent applications 176,804; 177,765; U.S. Pat. Nos. 4,659,652; 5,066,575; and 5,250,400.

Couplers that form yellow dyes upon reaction with oxidised and colour developing agent are described in such representative patents and publications as: U.S. Pat. Nos. 2,875,057; 2,407,210; 3,265,506; 2,298,443; 3,048,194; 3,447,928; 3,960,570; 4,910,126 and 5,340,703 and "Farbkuppler—Eine Literature Ubersicht," published in Agfa Mitteilungen, Band III, pp. 112–126 (1961). Such couplers are typically open chain ketomethylene compounds. Also preferred are yellow couplers such as described in, for example, European Patent Application Nos. 482,552; 510,535; 524,540; 543,367; and U.S. Pat. No. 5,238,803. For improved colour reproduction, couplers which give yellow dyes that cut off sharply on the long wavelength side are particularly preferred (for example, see U.S. Pat. No. 5,360,713).

Couplers that form colourless products upon reaction with oxidised colour developing agent are described in such representative patents as: U.K. Patent No. 861,138; U.S. Pat. Nos. 3,632,345, 3,928,041, 3,958,993 and 3,961,959. Typically such couplers are cyclic carbonyl containing compounds that form colourless products on reaction with an oxidised colour developing agent.

Couplers that form black dyes upon reaction with oxidised colour developing agent are described in such representative patents as U.S. Pat. Nos. 1,939,231; 2,181,944; 2,333,106 and 4,126,461; German OLS No. 2,644,194 and German OLS No. 2,650,764. Typically, such couplers are resorcinols or m-aminophenols that form black or neutral products on reaction with oxidised colour developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3-position may be employed. Couplers of this type are described, for example, in U.S. Pat. Nos. 5,026,628, 5,151,343 and 5,234,800.

It may be useful to use additional couplers any of which may contain known ballasts or coupling-off groups such as those described in U.S. Pat. Nos. 4,301,235, 4,853,319 and 4,351,897. The coupler may contain solubilising groups such as described in U.S. Pat. No. 4,482,629. The coupler may also be used in association with "wrong" coloured couplers (e.g. to adjust levels of interlayer correction) and, in colour negative applications, with masking couplers such as those described in EP 213.490; Japanese Published Application 58-172,647; U.S. Pat. Nos. 2,983,608, 4,070,191 and 4,273,861; German Applications DE 2,706,117 and DE 2,643,965; UK Patent No. 1,530,272 and Japanese Application 58-113935. The masking couplers may be shifted or blocked, if desired.

Typically, couplers are incorporated in a silver halide emulsion layer in a mole ratio to silver of 0.05 to 1.0 and generally 0.1 to 0.5. Usually the couplers are dispersed in a high-boiling organic solvent in a weight ratio of solvent to coupler of 0.1 to 10.0 and typically 0.1 to 2.0, although dispersions using no permanent coupler solvent are sometimes employed. The invention may be practised with any permanent high-boiling solvent known to be useful in the art, such as an aryl ester, such as dibutyl phthalate, diundecyl phthalate; phenols, such as p-dodecyl phenol, 2,4-di-isoamyl phenol: phosphates, such as trihexyl phosphate and tricresyl phosphate; alcohols, such as oleyl alcohol and hexadecanol and amides such as diethyldodecanamide and dibutylactanilide.

The resulting organic solution may then be mixed with an aqueous gelatin solution and the mixture passed through a mechanical mixing device suitable for high-shear or turbulent mixing generally suitable for preparing photographic emulsified dispersions, such as a colloid mill, homogenizer, microfluidizer, high-speed mixer, ultrasonic dispersing apparatus, blade mixer, device in which a liquid stream is pumped at high pressure through an orifice or interaction chamber, Gaulin mill or blender to form small particles of the organic phase suspended in the aqueous phase. More than one type of device may be used to prepare the dispersions. The auxiliary organic solvent may then removed by evaporation, noodle washing, or membrane dialysis. The dispersion particles preferably have an average particle size of less than 2 $\mu$m, generally from about 0.02 to 2 $\mu$m, more preferably from about 0.02 to 0.5 $\mu$m especially from about 0.02 to 0.3 $\mu$m. These methods are described in detail in U.S. Pat. Nos. 2,322,027, 2,787,544, 2,801,170, 2,801,171, 2,949,360 and 3,396,027.

Examples of suitable auxiliary solvents which can be used in the present invention include: ethyl acetate, isopropyl acetate, butyl acetate, ethyl propionate, 2-ethoxyethylacetate, 2-(2-butoxyethoxy)ethyl acetate, dimethylformamide, 2-methyl tetrahydrofuran, triethylphosphate, cyclohexanone, butoxyethyl acetate, methyl isobutyl ketone, methyl acetate, 4-methyl-2-pentanol, diethyl carbitol, 1,1,2-trichloroethane and 1,2-dichloropropane.

The aqueous phase of the coupler dispersions for use in the invention preferably comprises gelatin as a hydrophilic colloid. This may be gelatin or a modified gelatin such as acetylated gelatin, phthalated gelatin or oxidized gelatin. Gelatin may be base-processed, such as lime-processed gelatin, or may be acid-processed, such as acid-processed ossein gelatin. Other hydrophilic colloids may also be used, such as a water-soluble polymer or copolymer including, but not limited to poly(vinyl alcohol), partially hydrolyzed poly(vinyl acetate-co-vinyl alcohol), hydroxyethyl cellulose, poly(acrylic acid), poly(1-vinylpyrrolidone), poly (sodium styrene sulfonate), poly(2-acrylamido-2-methane sulfonic acid) and polyacrylamide. Copolymers of these polymers with hydrophobic monomers may also be used.

A surfactant may be present in either the aqueous phase or the organic phase or the dispersions can be prepared without any surfactant present.

Surfactants may be cationic, anionic, zwitterionic or nonionic. Ratios of surfactant to liquid organic solution typically are in the range of 0.5 to 25 wt. % for forming small particle photographic dispersions. In a preferred embodiment of the invention, an anionic surfactant is contained in the aqueous gelatin solution. Particularly preferred surfactants which are employed in the present invention include an alkali metal salt of an alkarylene sulfonic acid, such as the sodium salt of dodecyl benzene sulfonic acid or sodium salts of isopropylnaphthalene sulfonic acids, such as mixtures of di-isopropyl- and tri-isopropylnaphthalene sodium sulfonates; an alkali metal salt of an alkyl sulfuric acid, such as sodium dodecyl sulfate; or an alkali metal salt of an alkyl sulfosuccinate, such as sodium bis (2ethylhexyl) succinic sulfonate.

The materials for use in the invention may be used in association with materials that accelerate or otherwise modify the processing steps e.g. of bleaching or fixing to improve the quality of the image. Bleach accelerator releasing couplers such as those described in EP 193,389; EP 301,477 and in U.S. Pat. Nos. 4,163,669, 4,865,956 and 4,923,784, may be useful. Also contemplated is use of the compositions in association with nucleating agents, development accelerators or their precursors (UK Patent Nos. 2,097,140 and 2,131,188); electron transfer agents (U.S. Pat. Nos. 4,859,578 and 4,912,025); antifogging and anti colour-mixing agents such as derivatives of hydroquinones, aminophenols, amines, gallic acid; catechol; ascorbic acid; hydrazides; sulfonamidophenols and non colour-forming couplers.

The materials for use in the invention may also be used in combination with filter dye layers comprising colloidal silver sol or yellow, cyan and/or magenta filter dyes, either as oil-in-water dispersions, latex dispersions or as solid particle dispersions. Additionally, they may be used with "smearing" couplers (e.g. as described in U.S. Pat. Nos. 4,366,237, 4,420,556, 4,543,323 and in EP 96,570) Also, the compositions may be blocked or coated in protected form as described, for example, in Japanese Application 61/258,249 or U.S. Pat. No. 5,019,492.

The materials for use in the invention may further be used in combination with image-modifying compounds such as "Developer Inhibitor-Releasing" compounds (DIRs). DIRs useful in conjunction with the compositions of the invention are known in the art and examples am described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346,899; 362,870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Bane, J. R Thirtle and P. W. Vittum in Photographic Science and Engineering, Vol.13, p.174 (1969). Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, tellurotetrazoles or benzisodiazoles. In a preferred embodiment, the inhibitor moiety or group is selected from the following formulae:

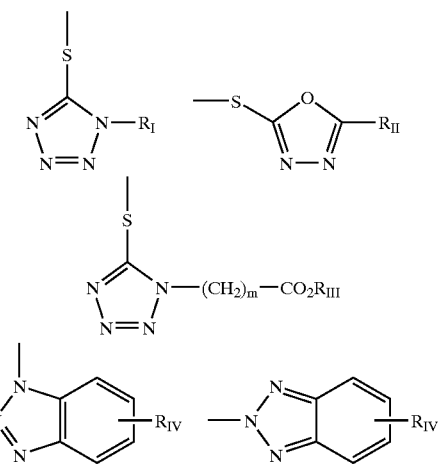

wherein $R_I$ is selected from the group consisting of straight and branched alkyls of from 1 to about 8 carbon atoms, benzyl, phenyl and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different colour as one associated with a different film layer. It may also be useful that the coupler moiety included in the developer inhibitor-releasing coupler forms colourless products and/or products that wash out of the photographic material during processing (so-called "universal" couplers).

As mentioned, the developer inhibitor-releasing coupler may include a timing group, which produces the time-delayed release of the inhibitor group, such as groups using an intramolecular nucleophilic substitution reaction (U.S. Pat. No. 4,248,962); groups utilising an electron transfer reaction along a conjugated system (U.S. Pat. Nos.4,409, 323, 4,421,845 and 4,861,701 and Japanese Applications 57-188035; 58-98728; 58-209736; 58-209738); groups utilizing ester hydrolysis (German Patent Application (OLS) No. 2,626,315); groups that function as a coupler or reducing agent after the coupler reaction (U.S. Pat. Nos. 4,438, 193 and 4,618,571) and groups that combine the features described above. It is typical that the timing group is of one of the formulae:

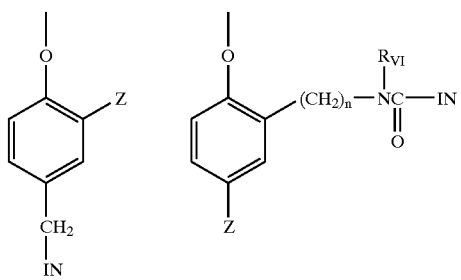

wherein IN is the inhibitor moiety, Z is selected from the group consisting of nitro, cyano, alkylsulfonyl; sulfamoyl (—SO$_2$NR$_2$) and sulfonamido (—NRSO$_2$R) groups; n is 0 or 1; and R$_{VI}$ is selected from the group consisting of substituted and unsubstituted alkyl and phenyl groups. The oxygen atom of each timing group is bonded to the coupling-off position of the respective coupler moiety of the DIAR.

The timing or linking groups may also function by electron transfer down an unconjugated chain. Linking groups are known in the art under various names. Often they have been referred to as groups capable of utilising a hemiacetal or iminoketal cleavage reaction or as groups capable of utilising a cleavage reaction due to ester hydrolysis such as U.S. Pat. No. 4,546,073. This electron transfer down an unconjugated chain typically results in a relatively fast decomposition and the production of carbon dioxide, formaldehyde or other low molecular weight by-products. The groups are exemplified in EP 464,612, EP 523,451, U.S. Pat. No. 4,146,396, Japanese Kokai 60-249148 and 60-249149.

It is also contemplated that the concepts of the present invention may be employed to obtain reflection colour prints as described in *Research Disclosure*, November 1979, Item 18716, available from Kenne Mason Publications, Ltd, Dudley Annex, 12a North Street, Emsworth, Hampshire P0101 7DQ, England Materials of the invention may be coated on pH adjusted support as described in U.S. Pat. No. 4,917,994; on a support with reduced oxygen permeability (EP 553,339); with epoxy solvents (EP 64,961); with nickel complex stabilisers (U.S. Pat. Nos. 4,346,165, 4,540,653 and 4,906,559 for example); with ballasted chelating agents such as those in U.S. Pat. No. 4,994,359 to reduce sensitivity to polyvalent cations such as calcium and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072, 633; 90-072,634; 90-077,822; 90-078,229; 90-078,230, 90-079,336; 90-079,337; 90-079,338; 90-079,690; 90-079, 691; 90-080,487; 90-080,488; 90-080,489; 90-080,490; 90-080,491; 90-080,492; 90-080,494; 90-085,928; 90-086, 669; 90-086,670; 90-087,360; 90-087,361; 90-087,362; 90-087,363; 90-087,364; 90-088,097; 90-093,662; 90-093, 663; 90-093,664; 90-093,665; 90-093,666; 90-093,668; 90-094,055; 90-094,056; 90-103,409; 83-62,586 and 83-09, 959.

Any silver halide combination can be used for the photographic element, such as silver chloride, silver chlorobromide, silver chlorobromoiodide, silver bromide, silver bromoiodide, or silver chloroiodide. In cases where the emulsion composition is a mixed halide, the minor component may be added in the crystal formation or after formation as part of the sensitisation or melting. The shape of the silver halide emulsion grain can be cubic, pseudo-cubic, octahedral, tetradecahedral or tabular. The emulsions may be precipitated in any suitable environment such as a ripening environment, a reducing environment or an oxidising environment.

Photographic elements can be exposed to actinic radiation, typically in the visible region of the spectrum, to form a latent image and can then be processed to form a visible dye image. Processing to form a visible dye image includes the step of contacting the element with a colour developing agent to reduce developable silver halide and oxidise the colour developing agent. Oxidised colour developing agent in turn reacts with the coupler to yield a dye.

With negative-working silver halide, the processing step described above provides a negative image. The described elements can be processed in the known Kodak C-41™ colour process as described in The British Journal of Photography Annual of 1988, pp 191–198. Where applicable, the element may be processed in accordance with colour print processes such as the RA-4™ process of Eastman Kodak Company as described in the British Journal of Photography Annual of 1988, pp 198–199. Such negative working emulsions are typically sold with instructions to process using a colour negative method such as the C-41™ or RA-4™ process. To provide a positive (or reversal) image, the colour development step can be preceded by development with a non-chromogenic developing agent to develop exposed silver halide, but not form dye, and followed by uniformly fogging the element to render unexposed silver halide developable. Such reversal emulsions are typically sold with instructions to process using a colour reversal process such as E-6™. Alternatively, a direct positive emulsion can be employed to obtain a positive image.

The multicolour photographic elements of the invention may be processed alternatively in a developer solution that will provide reduce processing times of one minute or less (dry to dry), and particularly reduced colour development times of less than about 25 seconds, such that all colour records are fully developed with aim sensitometry.

Preferred colour developing agents are p-phenylenediamines such as:

4-amino-NN-diethylaniline hydrochloride,
4-amino-3-methyl-N,N-diethylaniline hydrochloride,
4-amino-3-methyl-N-ethyl-N-(2-methanesulfonamidoethyl) aniline sesquisulfate hydrate,
4-amino-3-methyl-N-ethyl-N-(2-hydroxyethyl)aniline sulfate,
4-amino-3-(2-methanesulfonamido-ethyl)-N,N-diethylaniline hydrochloride and
4-amino-N-ethyl-N-(2-methoxyethyl)-m-toluidine di-p-toluene sulfonic acid.

Development is usually followed by the conventional steps of bleaching, fixing or bleach-fixing, to remove silver or silver halide, washing and drying.

The coupler dispersions may be coated with emulsions to form photographic elements at very low levels of silver (less than 100 mg/m$^2$). Reasons for doing this include reducing cost, reducing the thickness of silver halide emulsion layers to gain sharpness advantages and reducing the environmental impact during and after processing.

One class of low silver photographic material is colour material intended for redox amplification processes wherein the developed silver acts as a catalyst to the formation of the dye image. This process can take place in a low volume thin processor, such as a low volume thin tank (LVTT), for example, as disclosed in U.S. Pat. No. 5,436,118. Redox amplification processes have been described for example in GB 1,268,126, GB 1,399,481, GB 1,403,418, GB 1,560,572, U.S. Pat. Nos. 3,748,138, 3,822,129 and 4,097,278. In such processes, colour materials are developed to produce a silver image (which may contain only small amounts of silver) and are then treated with a redox amplifying solution (or a combined developer-amplifier) to form a dye image.

The following examples illustrate the invention but are not to be construed as to be limiting of the scope thereof. The preparative example is typical of the synthesis of any of the couplers, which can be prepared analogously by appropriate selection of reactants.

EXAMPLES

Preparative Examples
Synthesis of a Coupler of Formula (I) (I-1)
A. Preparation of 2-(3,4-Dichlorobenzamido)-4-chloro-5-aminophenol (4)

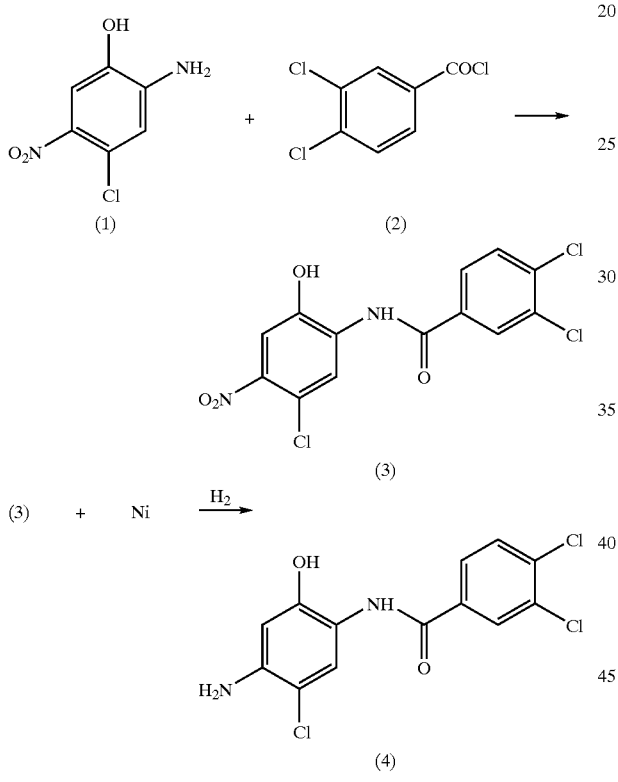

2-(3,4-dichlorobenzamido)-4-chloro-5-nitrophenol (3)

3,4-dichlorobenzoyl chloride (2) (38.0 g, 0.18 mol) was added to a stirred slurry of 2-amino-4-chloro-5-nitrophenol (1) (34.0 g, 0.18 mol) in ethyl acetate (250 ml) and the mixture refluxed for 2 h. After cooling the precipitate was filtered and then slurried in hot ethyl acetate (200 ml) and filtered again to give 50 g (77%) 2-(3,4-dichlorobenzamido)-4-chloro-5-nitrophenol (3).

2-(3,4-Dichlorobenzamido)-4-chloro-5-aminophenol (4)

The nitrophenol (3) (36.0 g, 0.1 mol) was dissolved in ethyl acetate (250 ml) and dimethylformamide (DMF) (50 ml). The solution was hydrogenated over Raney Nickel at 3040 kPa (30 atm)/25 C. for 15 h. The catalyst was removed by filtration through a pad of Kieselguhr and the ethyl acetate removed in vacuo. The residual solution of aminophenol (4) in DMF was poured on to an ice/water mixture (1.51) to precipitate aminophenol (4) (27 g, yield 84%), which was collected by filtration and dried. This was stored under a blanket of nitrogen while the ballast acid chloride was prepared.

B. Preparation of 2-(4-N-Methyl-N-butanesulphonamido) phenoxytetradecanoyl chloride (8)

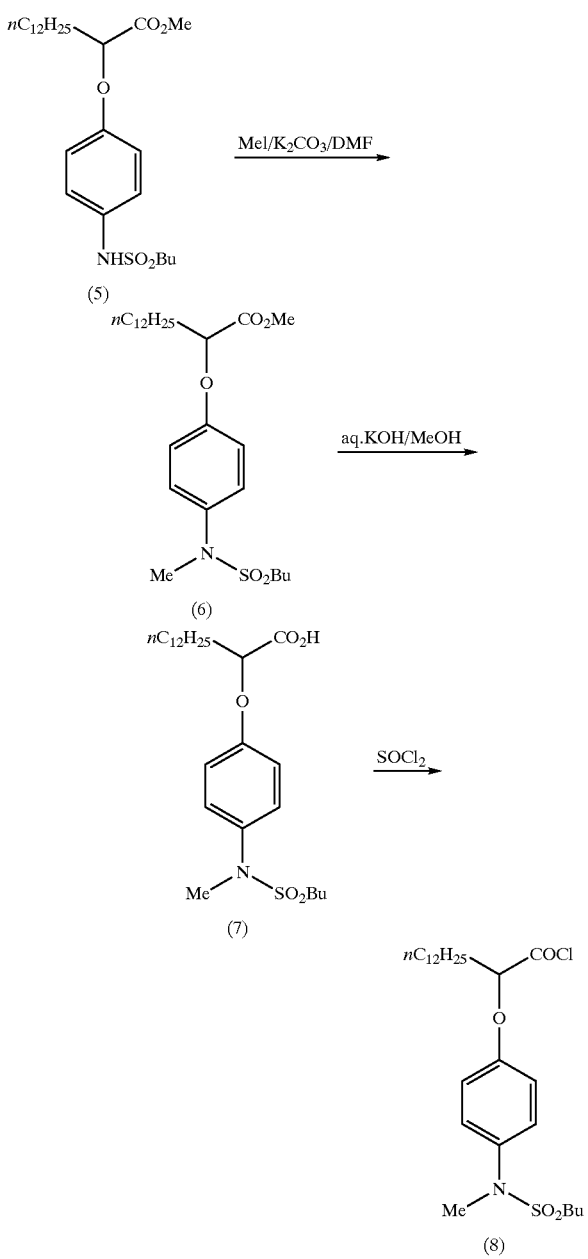

Methyl 2-(4-N-methyl-N-butanesulfonamido) phenoxytetradecanoate (6)

A solution in DMF (200 ml) of the ballast ester (5) (50.0 g, 0.1 mol), prepared as described in U.S. Pat. No. 5,972,587, was stirred at room temperature with solid potassium carbonate (27.6 g, 0.2 mol) while a solution of iodomethane (42.6 g, 0.3 mol) in DMF (50 ml) was dripped in over 0.5 h. When addition was complete, the reaction mixture was heated on a steam bath for 1 h then cooled and solvent removed under reduced pressure. The residue was partitioned between ethyl acetate and dilute hydrochloric acid (300 ml each) and the organic phase separated and dried over magnesium sulfate. Removal of ethyl acetate gave the crude product as a yellow oil which was purified by silica gel column chromatography (4:1 v/v 60–80 petrol/ethyl acetate),to give (6) as a colourless oil which rapidly solidified to a white solid on standing, 43.5 g (85%).

HPLC gave 100% purity for (6) whose correct structure was confirmed by nmr and mass spectra.

2-(4-N-Methyl-N-butanesulfonamido) phenoxytetradecanoic acid (7)

The ester (6) (56.0 g, 0.12 mol) was taken up in a mixture of methanol (300 ml) and tetrahydrofuran (THF) (50 ml). A solution of excess potassium hydroxide (19.5 g, 0.36 mol) in water (50 ml) was added in one charge and the solution stirred at room temperature for 1.5 h. The solvent was removed to about ⅓ original volume and the residue carefully poured onto a well stirred mixture of ice-water (2 l) containing concentrated hydrochloric acid (50 ml). Product acid (7) was obtained as a white solid after filtration and oven drying, 56.0 g (quantitative).

The structure of (7) was confirmed by ir, nmr and mass spectra.

2-(4-N-Methyl-N-butanesulphonamido) phenoxytetradecanoyl chloride (8)

The ballast acid (7) (33.0 g, 0.07 mol) was refluxed in excess thionyl chloride (150 ml) for 0.5 h. After cooling, the solution was evaporated to dryness and dichloromethane (150 ml) added followed by further evaporation to give the acid chloride (8) as a brown oil (~35 g, assumed quantitative).

The crude acid chloride was used immediately and without further purification for the synthesis of Coupler I-1.

C. Preparation of Coupler I-1

2-(3,4Dichlorobenzamido)-4-chloro-5-aminophenol (3) (20.0 g, 0.06 mol) was stirred in a mixture of DMF (50 ml) and tetrahydrofuran (THF) (150 ml) while N,N-dimethylaniline (20 ml) was added. The freshly prepared ballast acid chloride (8) (35 g, 0.07 mol) in THF (50 ml) was then added dropwise and the solution stirred at ambient temperature for 2 h. The solvent was removed in vacuo and the residue taken up in ethyl acetate (300 ml). The organic solution was washed successively with dilute hydrochloric acid and water then separated and dried over magnesium sulfate. Removal of solvent gave the crude coupler which was recrystallised (×3) from acetonitrile to give a I-1 as a clean white solid, 15.0 g, (32%), mp 139–141 C.

HPLC gave 100% purity for the coupler I-1 whose structure was confirmed by ir, nmr and mass spectra.

PHOTOGRAPHIC EXAMPLES

Dispersion Examples

Inventive couplers I-1 and I-2 were compared with comparison couplers CC-1 and CC-2, having the structures below:

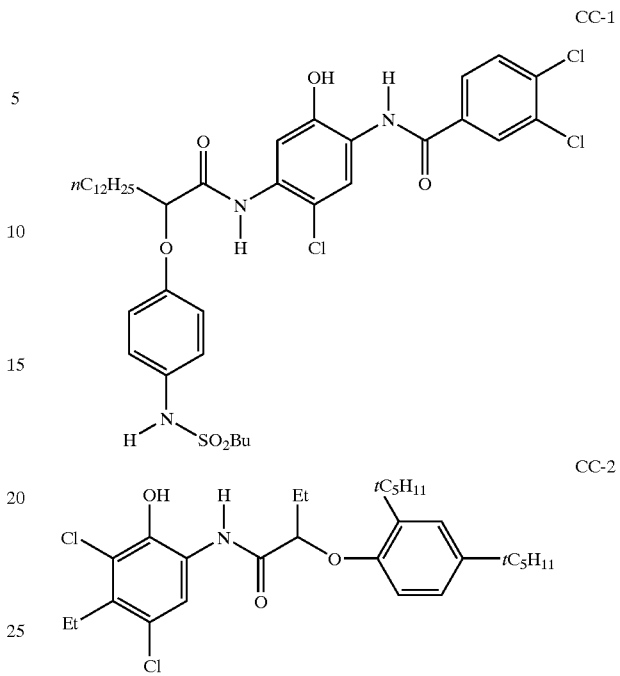

CC-1 was dispersed in gelatin according to the following procedure:

Coupler CC-1(5.59 g, 6.88 mmol) was dissolved in a mixture of p-dodecyl phenol (pDP) (2.8 g) and ethyl acetate (2 g). The mixture was heated to effect solution. After adding aqueous gelatin (40 g, 10%) containing 0.25% di-iso-propylnaphthalene sulfonic acid (sodium salt) surfactant at 60 C., the mixture was dispersed by ultrasonic agitation for 2 min. using a Dawe Instruments "Soniprobe" and diluted to 50 g with water. The completed dispersion was labelled Dispersion 1.

Dispersions 2 and 3, incorporating the inventive couplers I-1and I-2, were prepared in like manner. The same molar quantities of each coupler were used and the weights of pDP permanent coupler solvent were adjusted in proportion to the weight of coupler taken. The schedule is indicated below:

| Dispersion | Coupler | Coupler Weight | pDP Weight | EtOAc Weight |
| --- | --- | --- | --- | --- |
| 1 | CC1 | 5.29 g | 2.64 g | 2.0 g |
| 2 | I-1 | 5.38 g | 2.69 g | 2.0 g |
| 3 | I-2 | 5.48 g | 2.74 g | 2.0 g |

A further comparison coupler CC-2 was also dispersed in a similar fashion, except that dibutyl phthalate (dBP) was used as the permanent coupler solvent in place of pDP. For this dispersion, the oil phase component weights were:

| Dispersion | Coupler | Coupler Weight | dBP Weight | EtOAc Weight |
| --- | --- | --- | --- | --- |
| 4 | CC2 | 3.50 g | 1.75 g | 2.0 g |

Each of the above dispersions was further diluted to 300 g with an appropriate quantity of aqueous gelatin and mixed with a red-sensitive cubic silver chloride photographic emulsion (average edge length: 0.36 µm) before coating on a resin-coated paper support carrying a precoated gel pad (3 g.m$^{-2}$). A protective gelatin supercoat (1.0 g.m$^{-2}$), containing an appropriate quantity of bis-(vinyl-sulfonylmethyl) ether hardener, was applied over the photosensitive layer. The silver and coupler coverages were, respectively, 0.21 g.m$^{-2}$ and 0.831 mmol.m$^{-2}$. The coating structure is shown below.

| Resin Coated Paper | | |
|---|---|---|
| Gel | 1.0 g.m$^{-2}$ | GEL SUPERCOAT |
| Hardener* | 0.084 g.m$^{-2}$ | |
| Coupler | 0.831 mM.m$^{-2}$ | PHOTOSENSITIVE LAYER |
| Ag | 0.21 g.m$^{-2}$ | |
| Gel | 1.615 g.m$^{-2}$ | |
| Gel | 3.0 g.m$^{-2}$ | GEL PAD |

*Hardener = bis(vinylsulphonylmethyl) ether

Sample strips of the coatings were exposed through a step tablet (density range 0–3, 0.15 inc.) and developed through stndard KODAK RA4™ process solutions. Sensitometric curves were generated for each coating and the spectral absorption characteristics of the image dyes were also measured. The thermal stability of the image dyes was monitored in an accelerated dark keeping test at 75 C., 50% RH, while image dye light stability was assessed using standard simulated daylight fading equipment incorporating a Xenon arc source, delivering an exposure intensity of 50 Klux at the sample plane. For the latter tests, sample strips were mounted in the fader under a UV-absorbing filter, comprising Tinuvin™-328 (Ciba-Geigy), dispersed in gelatin and coated on a transparent polyester sheet at a coverage of 1.0 g.m–2. At the end of these tests, the sensitometric curves were re-read and compared with the initial curves. Status "A" red density losses from an initial value of 1.0 were recorded.

The results are reproduced in the TABLE, which shows the yellowing and density loss from 1.0 for each of the stability tests, as well as the maximum developed density and the wavelength of maximum absorption of the image dye. This figure, read from the measured spectral absorption curves of developed patch of density near 1.0, is a convenient representation of the image dye hue.

TABLE

Image Dye Hue and Stability Data

| Coated Dispersion | $D_{max}$ | $\lambda_{max}$ (nm) | Light Stability* $\Delta D_{1.0}$ | Dark Stability† $\Delta D_{1.0}$ |
|---|---|---|---|---|
| 2. (I-1) | 2.445 | 661 | −0.27 | 0.00 (Inv) |
| 3. (I-2) | 2.359 | 660 | −0.25 | −0.03 (Inv.) |
| 1. (CC1) | 2.241 | 662 | −0.40 | −0.03 (Comp.) |
| 4. (CC2) | 2.309 | 663 | −0.32 | −0.23 (Comp.) |

*6 wk, 50 klux Fade, $\Delta D_{1.0}$ = Density loss from 1.0
†6 wk 75 C, 50% RH, $\Delta D_{1.0}$ = Density loss from 1.0

The results show that the couplers I-1 and I-2 of this invention are comparable in activity to the comparison couplers CC1 and CC2, and give dyes with adequately deep hue. The thermal dark stability of the image dye from the comparison coupler CC1 is good, and superior to that of the comparison coupler CC2, but its light stability is poor. The dyes from the inventive couplers I-1 and I-2 remain the excellent dark stability displayed by the analogous dyes from CC1, and also demonstrate good light stability, superior to that of the image dye from CC2.

Comparison coupler CC2 is already well known as a commercially important component of photographic colour paper products and the image dyes from the inventive couplers are superior to those of CC2 in terms of resistance to decomposition by both light and heat.

The invention has been described in detail with particular reference to certain preferred embodiments thereof, but it will be understood that variations is and modifications can be effected within the claims of the invention.

What is claimed is:

1. A photographic element comprising at least one silver halide emulsion layer having associated therewith a phenolic cyan dye-forming coupler of formula (I)

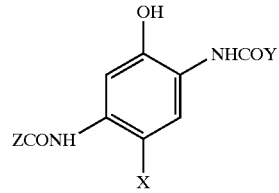

(I)

wherein
X is hydrogen or a group that can be split off by the reaction of the coupler with an oxidised colour developing agent, and
Z is the group

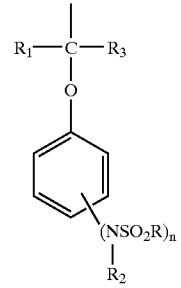

wherein
each R is independently an unsubstituted or substituted alkyl or aryl group or a 5–10 membered heterocyclic ring which contains one or more heteroatoms selected from nitrogen, oxygen and sulfur, which ring is unsubstituted or substituted;
$R_1$ is hydrogen or an unsubstituted or substituted alkyl or aryl group,
$R_2$ is an unsubstituted or substituted alkyl or aryl group or a 5–10 membered heterocyclic ring which contains one or more heteroatoms selected from nitrogen, oxygen and sulfur, which ring is unsubstituted or substituted;
$R_3$ is hydrogen or an unsubstituted or substituted alkyl or aryl group,
n is 1 or 2, and each group —N($R_2$)$SO_2$R is in the ortho or para position with respect to the alkoxy group,
Y is a phenyl group substituted with more than one chloro, fluoro, trifluoromethyl, cyano, alkoxycarbonyl or alkylsulfonyl group, provided that (a) when $R_2$ is an unsubstituted benzyl group, n is 1 and —N($R_2$)$SO_2$R is in the ortho position with respect to the alkoxy group, R may not be a pyridyl group, and (b) at least one of R, $R_1$, $R_2$, X and Y or Z is or includes ballast group.

2. A photographic element as claimed in claim 1 wherein Y is a phenyl group comprising two chloro substituents.

3. An elements as claimed in claim 2 wherein R, $R_1$ and $R_2$ are independently an unsubstituted or substituted alkyl group.

4. An element as claimed in claimed 3 wherein each of R and $R_2$ is a lower alkyl group.

5. An element as claimed in claim 2 wherein $R_1$ is an alkyl group having at least 8 carbon atoms.

6. An element as claimed in claim 2 wherein $R_3$ is hydrogen.

7. An element as claimed in claim 2 wherein n is 1 and the group —$N(R_2)SO_2R$ is in the para position with respect to the alkoxy group.

8. An element as claimed in claim 1 wherein the cyan dye-forming coupler has the structure

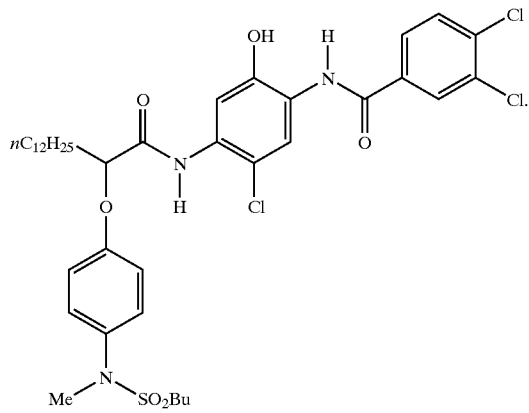

9. An element as claimed in claim 2 wherein the cyan dye-forming coupler has the structure

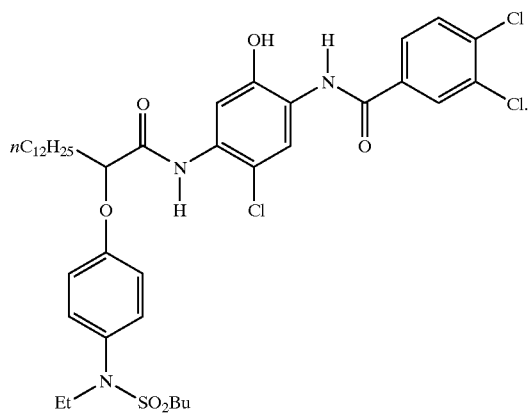

10. A multicolour photographic element comprising a support bearing yellow, magenta and cyan image-dye-forming units comprising at least one blue-, green- or red-sensitive silver halide emulsion layer having associated therewith at least one yellow, magenta or cyan dye-forming coupler respectively, wherein the element comprises at least one cyan dye-forming coupler of formula (I).

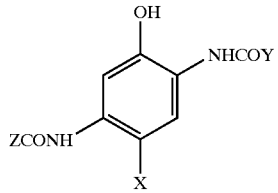

wherein

X is hydrogen or a group that can be split off by the reaction of the coupler with an oxidised colour developing agent, and Z is the group

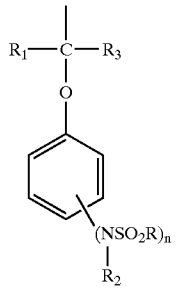

wherein each R is independently an unsubstituted or substituted alkyl or aryl group;

$R_1$ is hydrogen or an unsubstituted or substituted alkyl or aryl group, $R_2$ is an unsubstituted or substituted alkyl or aryl group or a 5–10 membered heterocyclic ring which contains one or more heteroatoms selected from nitrogen, oxygen and sulfur, which ring is or unsubstituted or substituted;

$R_3$ is hydrogen or an unsubstituted or substituted alkyl or aryl group, n is 1 or 2, and each –$N(R_2)SO_2R$ is in the ortho or para position with respect to the alkoxy group, Y is a phenyl group substituted with more than one chloro, fluoro, trifluoromethyl, cyano, alkoxycarbonyl or alkylsulfonyl group, provided that (a) when $R_2$ is an unsubstituted benzyl group, n is 1 and —$N(R_2)SO_2R$ is in the ortho position with to the alkoxy group, R may not be pyridyl group, and (b) at least one of R, $R_1$, $R_2$, X and Y or Z is or includes a ballast group.

* * * * *